United States Patent [19]

Bier, Jr.

[11] Patent Number: 4,938,222
[45] Date of Patent: Jul. 3, 1990

[54] THERAPEUTIC BANDAGE

[76] Inventor: John D. Bier, Jr., 635 Pear Tree Cir., Columbia, Mo. 65203

[21] Appl. No.: 325,901

[22] Filed: Mar. 20, 1989

[51] Int. Cl.$^5$ .............................................. A61F 7/00
[52] U.S. Cl. ...................................... 128/402; 128/382
[58] Field of Search ............... 128/402, 403, 392, 384, 128/82.16, 882, 400, 581; 62/530, 4; 126/204

[56] References Cited

U.S. PATENT DOCUMENTS

| | | | |
|---|---|---|---|
| 551,934 | 12/1895 | Weber | 128/403 |
| 1,473,506 | 11/1923 | Nessler | 128/402 |
| 3,889,689 | 6/1975 | Lebold | 128/402 |
| 4,044,773 | 7/1977 | Baldwin, III . | |
| 4,055,188 | 10/1977 | Pelton . | |
| 4,076,022 | 2/1978 | Walker | 128/82.1 |
| 4,214,588 | 7/1980 | Byler | 128/402 |
| 4,585,003 | 4/1986 | Meistrell | 128/402 |
| 4,592,358 | 6/1986 | Westplate | 128/402 |
| 4,753,240 | 6/1988 | Spartis | 128/379 |

Primary Examiner—Edward M. Coven
Assistant Examiner—Mark S. Graham
Attorney, Agent, or Firm—Leon Gilden

[57] ABSTRACT

A therapeutic bandage is set forth wherein the bandage is formed with an "L" shaped body including a quarter spherical relief opening at the exterior juncture of the vertical and horizontal legs of the "L" shaped body. The bandage includes a right and left forward edge to be overfolded an anatomical ankle of an individual including multi-directional fasteners pivotally mounted for securement to a plurality of positions. The fasteners utilize hook and loop fasteners for securement purposes.

1 Claim, 1 Drawing Sheet

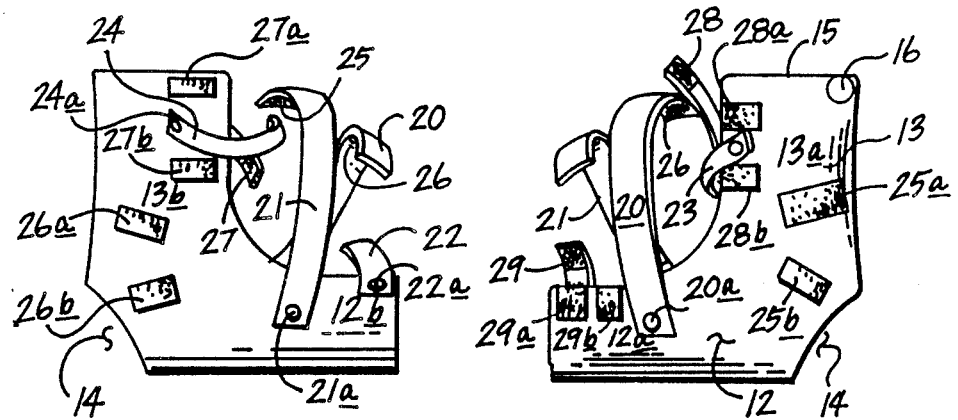
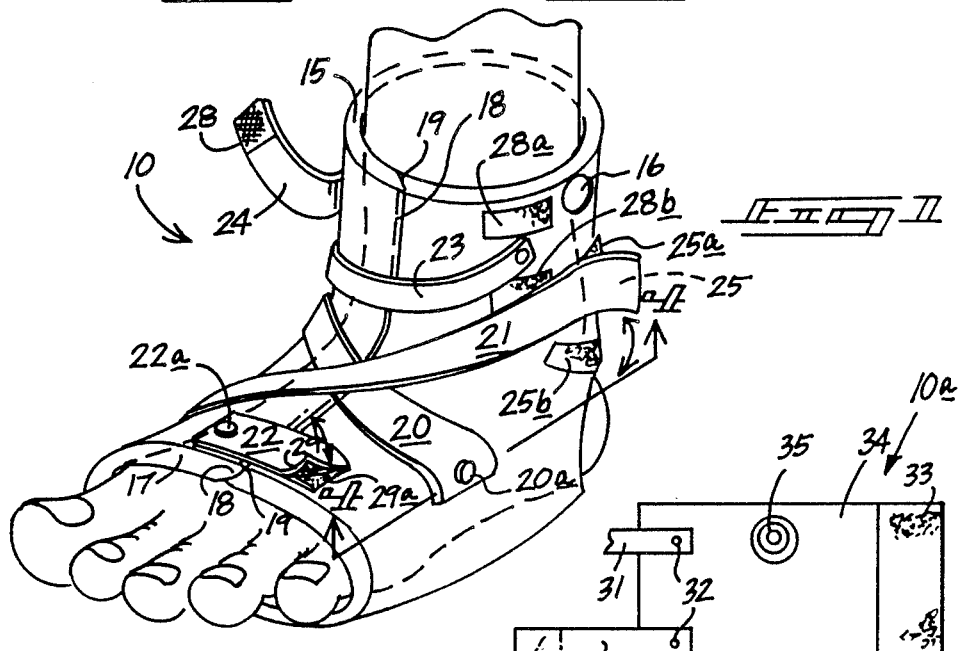
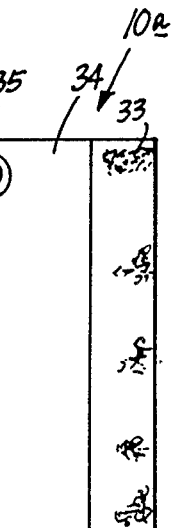
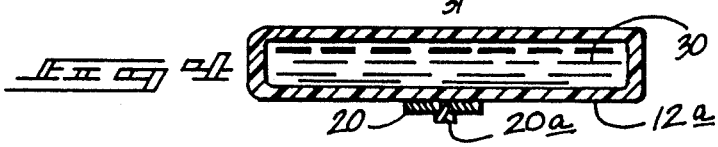

THERAPEUTIC BANDAGE

BACKGROUND OF THE INVENTION

1. Field of the Invention

The field of invention relates to therapeutic bandages, and more particularly pertains to a new and improved therapeutic bandage utilizing multi-directional fasteners to facilitate tensioning in various directions to control swelling of an individual joint.

2. Description of the Prior Art

The use of bandages and wraps of various types to accommodate swelling has been set forth in the prior art. The prior art has further utilized refrigerant secured within the wrap to further control swelling, as is utilized by the instant invention. Heretofore, however, the prior art has failed to set forth the use of multi-directional fasteners, as is present in in the instant invention, to control swelling in a differential manner. For example, U.S. Pat. No. 4,044,733 to Baldwin sets forth a polyurethane film formed with a hollow interior receiving water which may be frozen into a thin layer such that the layer may be cracked into fragments when the wrap is secured about an anatomical surface of an area to be treated.

U.S. Pat. No. 4,055,188 to Pelton sets forth a therapeutic wrap utilizing a resilient bandage with a refrigerant housed therewithin for securement about an individual, however the patent fails to provide the use of multi-directional fasteners and relies upon conventional clips to secure edges of the wrap wherein the wrap further only utilizes a refrigerant about a limited portion of the wrap thereby limiting the effective surface of the wrap to include a swelling retardant refrigerant.

U.S. Pat. No. 4,592,358 to Westplate sets forth a therapeutic wrap utilizing a compartmentalized array of packets secured to a strap that may be applied to various body portions. The wrap of the Westplate patent is typical of the prior art and its failure to provide multi-directional fastener members on the wrap once the wrap is positioned about a body part to assist in the reduction of swelling of an individual.

U.S. Pat. No. 4,625,729 to Roney sets forth an encircling cuff-like device fastenable about the wrist of an individual with a refrigerant gel therewithin. The Roney patent, as is typical of the prior art, fails to provide the use of pivotally mounted fasteners to adjust the direction of tensioning of the wrap when secured about an individual.

As such, it may be appreciated that there is a continuing need for a new and improved therapeutic wrap which addresses both the problems of ease of use and effectiveness in application, and in this respect, the present invention substantially fulfills this need.

SUMMARY OF THE INVENTION

In view of the foregoing disadvantages inherent in the known types of therapeutic wraps now present in the prior art, the present invention provides a therapeutic bandage wherein the same may be secured about an individual anatomical body part and is further provided with multi-directional fastening members to facilitate various tensioning orientations of the straps to assist in the controlling of swelling. As such, the general purpose of the present invention, which will be described subsequently in greater detail, is to provide a new and improved therapeutic bandage which has all the advantages of the prior art therapeutic wraps and none of the disadvantages.

To attain this, the present invention comprises a generally "L" shaped body for securement about an ankle or elbow portion of an individual formed with a vertical and horizontal leg with a quarter spherical recess at an exterior junction of the legs with a first co-extensive left and a second co-extensive right forward edge for encompassing the anatomical part wherein the plural pairs of multi-directional fasteners pivotally mounted to exterior surfaces of the bandage are securable to one of a plurality of fastening points utilizing hook and loop fasteners.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved therapeutic bandage which has all the advantages of the prior art therapeutic bandages and none of the disadvantages.

It is another object of the present invention to provide a new and improved therapeutic bandage which may be easily and efficiently manufactured and marketed.

It is a further object of the present invention to provide a new and improved therapeutic bandage which is of a durable and reliable construction.

An even further object of the present invention is to provide a new and improved therapeutic bandage which is susceptible of a low cost of manufacture with regard to both materials and labor, and which accordingly is then susceptible of low prices of sale to the consuming public, thereby making such therapeutic bandage economically available to the buying public.

Still yet another object of the present invention is to provide a new and improved therapeutic bandage which provides in the apparatuses and methods of the prior art some of the advantages thereof, while simultaneously overcoming some of the disadvantages normally associated therewith.

Still another object of the present invention is to provide a new and improved therapeutic bandage utilizing multi-directional fastening straps to assist in the controlling of swelling of the anatomical part and further including a refrigerant gel to control swelling.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention.

FIG. 2 is a left orthographic view taken in elevation of the instant invention.

FIG. 3 is a right orthographic view taken in elevation of the instant invention.

FIG. 4 is an orthographic view taken along the lines 4—3 of FIG. 1 in the direction indicated by the arrows.

FIG. 5 is a top orthographic view of a modified application of the instant invention.

DESCRIPTION OF THE PREFERRED EMBODIMENT

With reference now to the drawings, and in particular to FIGS. 1 to 5 thereof, a new and improved therapeutic bandage embodying the principles and concepts of the present invention and generally designated by the reference numerals 10 and 10a will be described.

More specifically, it will be noted that the therapeutic bandage apparatus 10 essentially comprises a hollow "L" shaped body 11 formed of flexible polyurethane film with heat seamed edges to effect configurational integrity to the "L" shaped configuration to conform the bandage to a desired anatomical part, such as an ankle, as illustrated in FIG. 1. The body is formed with a lower horizontal leg 12 and an upper vertical leg 13 defining a cuff-like surrounding member when secured about the body part to receive the body part, in particular the ankle, as illustrated in FIG. 1 therewithin. A quarter-spherical relief opening 14 is formed at the exterior intersection of the lower horizontal leg 12 and the upper vertical leg 13 to facilitate a heel of an individual directed therethrough. The lower horizontal leg 12 is formed with a left side 12a and a right side 12b wherein similarly the upper vertical leg 13 is formed with a left side 13a and a right side 13b that merge to form the "L" shaped body 11. A top edge 15 defines the upper terminal end of the upper vertical leg 13 wherein a forward edge 17 defines the forwardmost terminal end of the horizontal leg 12. A fill plug 16 is threadedly and selectively securable within the upper vertical leg 13 to enable a quantitative filling of the interior of the "L" shaped body.

The "L" shaped body 11 terminates in a right forward edge 18 and a left forward edge 19 continuously positional relative to one another to enable securement of the therapeutic bandage 10 about an ankle joint, as illustrated in FIG. 1.

The invention utilizes a series of multi-directional straps including a first directional strap 20 pivotally mounted at a first pivot 20a to the left side 12a of the body with a second directional strap 21 pivotally mounted at second pivot 21a on the right side 12b of the "L" shaped body 11. A third directional strap 22 pivotally mounted at third pivot 22c is mounted on the right side 12b of the lower horizontal leg 12 adjacent the forward edge 17 wherein the third pivot 22c is spaced inwardly of the forward edge 17 a distance substantially equal to half the width of the third directional strap 12. This enables attachment of the third directional strap 22 in alignment with the forward edge 17 in a first position or into a second position angulated inwardly along the seam created by the right and left forward edges 18 and 19 respectively in a manner to be discussed below. A fourth directional strap 23 is secured to the left side 13a of the upper vertical leg 13 about a fourth pivot 23a spaced below the top edge 15 of the upper vertical leg 13 a distance substantially equal to the width of the fourth directional strap 23. A fifth direction strap 24 is pivotally secured utilizing a fifth pivot 24a onto the right side 13b of the upper vertical leg 13 and spaced below the top edge 15 a distance also equal substantially to the width of the fifth directional strap 24.

The directional straps 20 through 24 are pivotally mounted onto the outer surface of the "L" shaped body 11 to enable multiple securement at a variety of angles to facilitate tensioning in differing directions to the "L" shaped body 11 and thusly control swelling when secured about an individual's joint or limb.

More particularly, the directional straps 20 through 24 utilize hook and loop fastening portions at terminal ends securable to one of a plurality of hook and loop fastening surfaces spacely positioned about the surface of the "L" shaped body 11.

The first directional strap 20 utilizes a first hook and loop fastening surface 26 multiply securable to either of a plurality of first patches 26a and 26b positioned overlying one another on the right side 13b of the upper vertical leg 13 spaced above the relief opening 14. The second hook and loop fastening surface 25 formed on the terminal end of the second directional strap 21 is securable to either of second patches 25a and 25b secured to on the left side 13a of the upper vertical leg 13 in opposed alignment to the first patches 26a and 26b wherein the second patches 25a and 25b are overlying each other in vertically spaced positioning above the relief opening 14 and spaced below the top edge 15. The third hook and loop fastening surface 29 formed at the interior terminal edge surface of the third directional strap 22 utilizes third patches 29a and 29b wherein the third patch 29a is positioned in alignment and adjacent the forward edge 17 of the lower horizontal leg 12 with the other of the third patches 29b positioned interiorly thereof spaced along the left forward edge 19. The fourth hook and loop fastening surface 27 formed on the interior terminal edge surface of the third directional strap 23 associates selectively securable to either of the fourth patches 27a and 27b positioned on the left side 13a of the upper vertical leg 13 with the upper fourth patch 27a positioned adjacent the top edge 15 with the other fourth patch 27b positioned underlying and spaced below the patch 27a. Similarly, the fifth hook and loop fastening surface 28 secured to the interior terminal edge surface of the fifth directional strap 24 is selectively securable to either of the fifth patches 28a and 28b positioned on the right side 13b of the upper vertical leg 13 in a similar orientation to the fourth patches 27a and 27b wherein the upper fifth patch 28a is positioned adjacent the top edge 15 with the other fifth patch 28b spaced vertically below and aligned with the upper patch 28a. Accordingly, it may be appreciated therefore that a multitude of variations and combinations of tensioning orientations may be available to facilitate a multiple tensioning and orientation of the "L" shaped body 11 about an individual body part.

The fill plug 16 enables filling of the hollow "L" shaped body 11 with a refrigerant gel comprised essentially of ethylene glycol and water which will freeze only into a slushy malleable mixture to enable accommodation of flexure of the individual anatomical body part.

Reference to FIG. 5 illustrates a further embodiment 10a of the therapeutic bandage wherein a series of directional straps 31 are pivotally mounted about pivots 32 utilizing hook and loop fastening surfaces 31a at terminal ends thereof for selective and multi-directional securement to the hook and loop fastening strip 33 secured at the other terminal side of the elongate body 34 which is also provided with a selectively removable fill plug 35 for introduction of a refrigerant gel interiorly of the body 34.

As to the manner of usage and operation of the instant invention, the same should be apparent from the above description and no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the U.S. is as follows:

1. A therapeutic bandage for securement about an individual foot member, comprising, an elongate flexible hollow body for encompassing an anatomical part of said individual including a nonhardening refrigerant contained therewithin, and said elongate body including a top edge surface and an opposed forward edge surface and further including a right side bounded by a continuous elongate right edge, and a left side bounded by a continuous elongate left edge, and first strap means mounted on said right side selectively securable to a plurality of patch members secured to said left side, and second strap means mounted on said left side selectively securable to a plurality of patch members secured to said right side, and wherein said first strap means is pivotally mounted to said right side and said second strap means is pivotally mounted to said left side, and wherein said first strap means includes a first strap, a second strap, and a third strap, and wherein each of said first, second, and third straps are securable to said patch members and said patch members include a plurality of patches selectively associatable with one of each of said first, second, and third straps, and wherein said second strap means includes a fourth strap and a fifth strap selectively securable to a plurality of respective fourth patches and fifth patches, and wherein a respective first, second, and third pivot member pivotally secures the respective first, second, and third straps of the right side, and a respective fourth and fifth pivot member secure the respective fourth and fifth straps to the left side, and wherein said flexible hollow body comprises an "L" shaped body and is formed with a quarter spherical relief opening defining an exterior intersection of a lower horizontal leg and an upper vertical leg forming said "L" shaped body, and wherein the quarter spherical relief opening is spaced from the right edge and left edge to receive a heel portion of the foot member therethrough, and wherein said first, second, and third straps are secured to the lower horizontal leg of the "L" shaped body, and wherein the fourth and fifth straps are secured to the upper vertical leg of the "L" shaped body, and wherein said "L" shaped body further includes a threadedly removable fill plug formed within an upper portion of the upper vertical leg for selective filling of a refrigerant gel within the "L" shaped body.

* * * * *